(12) United States Patent
Zook et al.

(10) Patent No.: US 8,574,256 B2
(45) Date of Patent: Nov. 5, 2013

(54) METHOD OF PERFORMING A SUPRAPUBIC TRANSURETHRAL CYSTOSTOMY

(75) Inventors: Ronald E. Zook, Bigfork, MT (US); Timothy E. Braun, Kalispell, MT (US); Kenneth A. High, Helena, MT (US); Laurence K. Sampson, Denver, CO (US); Steve W. Jackinsky, Denver, CO (US); Pete W. Kroehl, Denver, CO (US); Davey B. Palmer, Highlands Ranch, CO (US); David W. Wright, Littleton, CO (US); Paul P. Burek, Centennial, CO (US)

(73) Assignee: Swan Valley Medical, Incorporated, Big Fork, MT (US)

( * ) Notice: Subject to any disclaimer, the term of this patent is extended or adjusted under 35 U.S.C. 154(b) by 0 days.

(21) Appl. No.: 13/346,587

(22) Filed: Jan. 9, 2012

(65) Prior Publication Data
US 2012/0109175 A1 May 3, 2012

Related U.S. Application Data

(62) Division of application No. 12/238,941, filed on Sep. 26, 2008, now Pat. No. 8,118,826.

(60) Provisional application No. 60/975,548, filed on Sep. 27, 2007, provisional application No. 61/038,457, filed on Mar. 21, 2008.

(51) Int. Cl.
*A61B 17/34* (2006.01)

(52) U.S. Cl.
USPC .......................... 606/185; 606/170

(58) Field of Classification Search
USPC ............... 606/87, 96–98, 108, 170, 184, 185; 600/226, 228, 231, 234; 604/164.01, 604/164.06, 164.07, 164.08, 200–206
See application file for complete search history.

(56) References Cited

U.S. PATENT DOCUMENTS

| 5,334,185 A * | 8/1994 | Giesy et al. ............... 604/170.01 |
| 6,596,001 B2 * | 7/2003 | Stormby et al. ............... 606/144 |
| 2005/0143690 A1 * | 6/2005 | High ......................... 604/164.01 |

* cited by examiner

*Primary Examiner* — Thomas McEvoy
*Assistant Examiner* — Sarah W Aleman
(74) *Attorney, Agent, or Firm* — John R. Ley

(57) ABSTRACT

A suprapubic transurethral cystotomy apparatus and method of forming a surgical opening therewith. The apparatus includes an elongate tubular body including a proximal portion and a distal portion inclined relative to one another. The distal portion extends along an axis to an end configured for receipt through a urethra. An elongate arm has a first end operably attached to the proximal portion of the tubular body and a second end providing an indicator establishing an axis aligned coaxially with the axis of the distal portion. A surgical opening is formed with a cutting member being extended along the axis of the indicator.

21 Claims, 14 Drawing Sheets

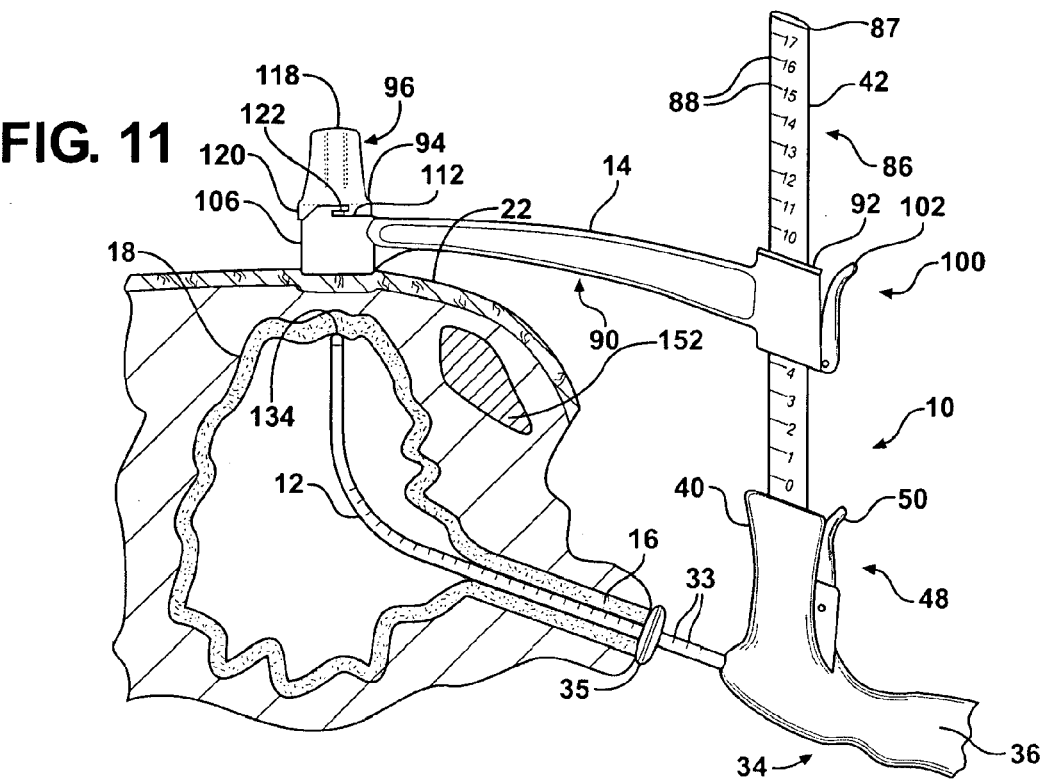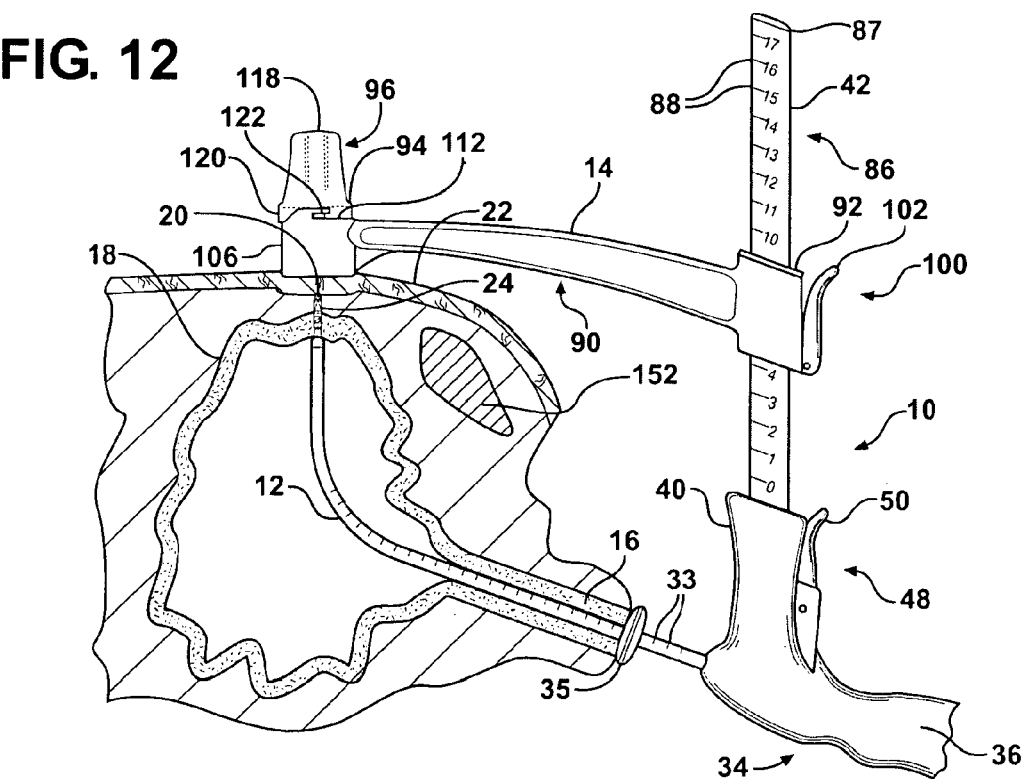

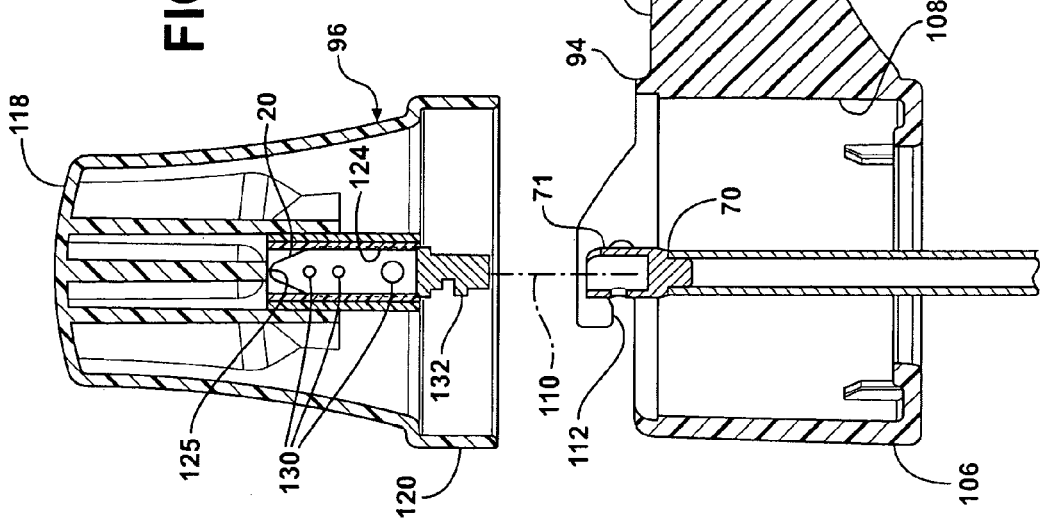
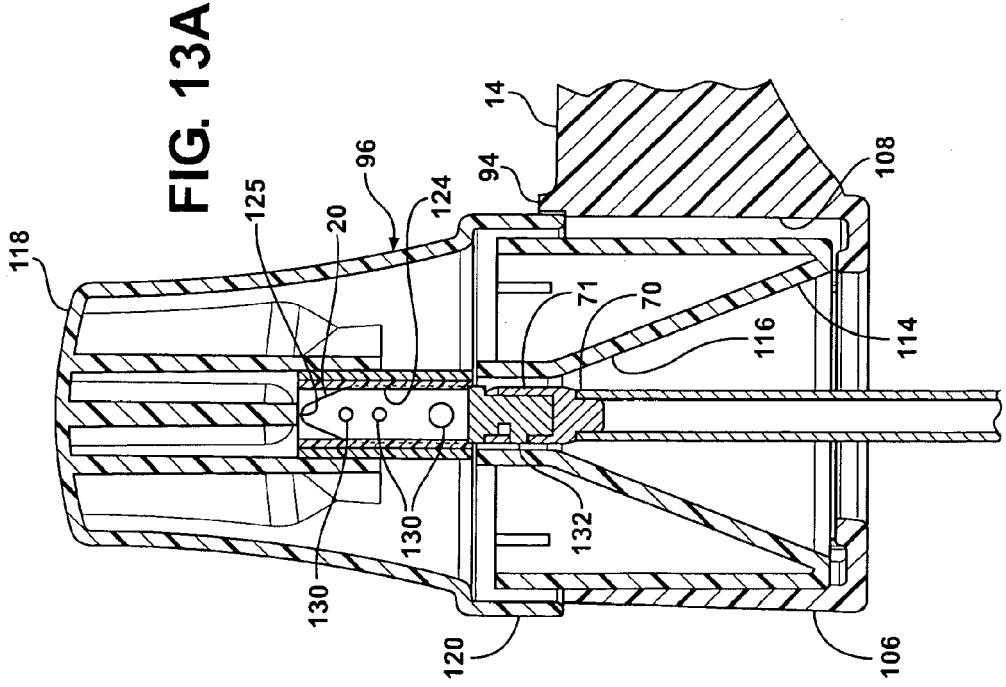

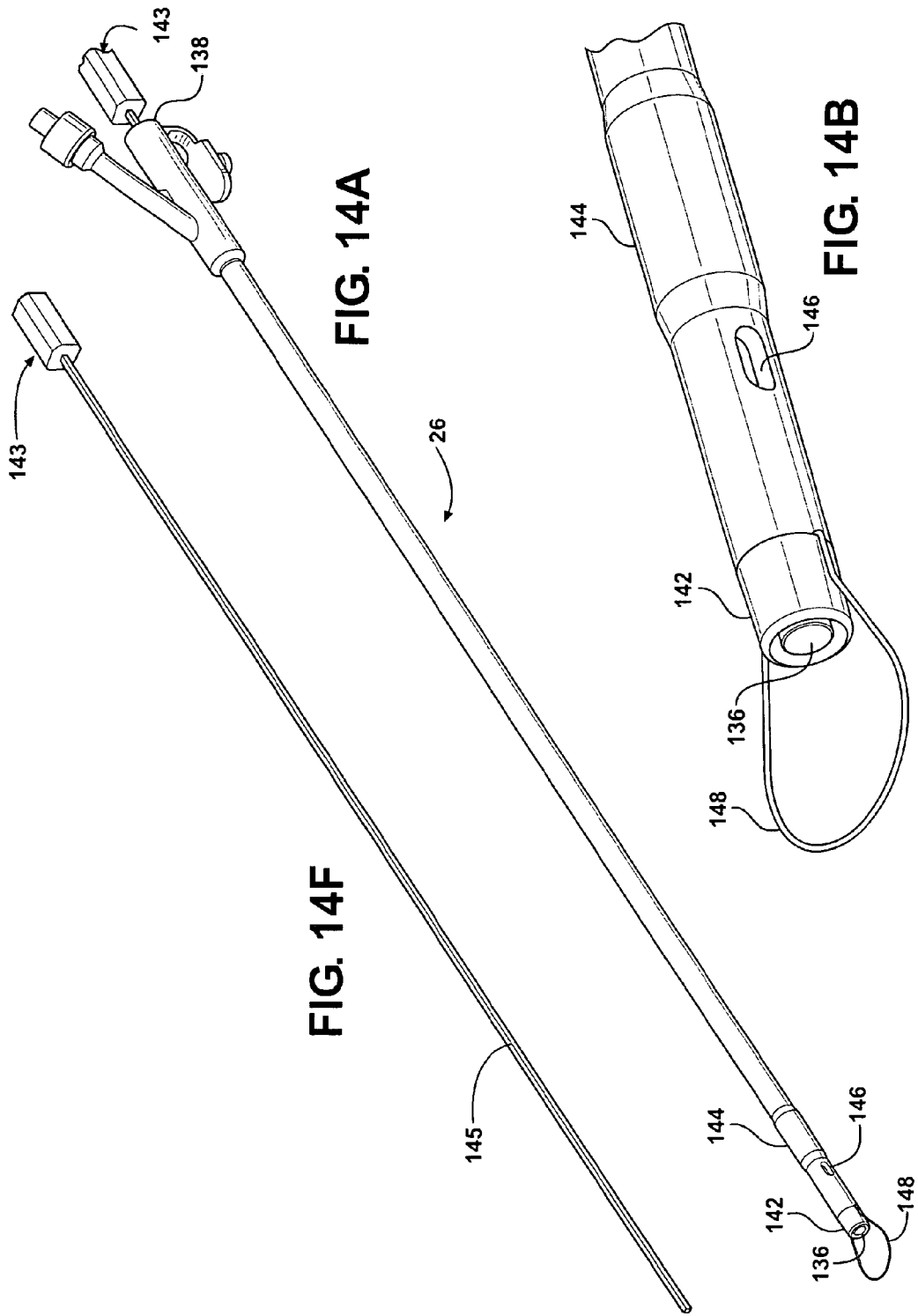

METHOD OF PERFORMING A SUPRAPUBIC TRANSURETHRAL CYSTOSTOMY

CROSS-REFERENCE TO RELATED APPLICATIONS

This application is a division of U.S. application Ser. No. 12/238,941, filed Sep. 26, 2008, now U.S. Pat. No 8,118,826, which claims the benefit of U.S. Provisional Application Ser. No. 60/975,548, filed Sep. 27, 2007, and U.S. Provisional Application Ser. No. 61/038,457, filed Mar. 21, 2008, all of which are incorporated herein by reference in their entirety.

BACKGROUND OF THE INVENTION

1. Technical Field

This invention relates generally to methods and apparatus for forming a surgical opening and providing guidance for an instrument while inside a body cavity with an external guidance apparatus, and more particularly to methods and apparatus for performing a transurethral (inside-out) suprapubic cystostomy, associated urological procedures and other surgical procedures.

2. Related Art

It is well known in the medical profession that many people experience bladder emptying problems (either urinary retention, or urinary incontinence). When severe, both conditions require drainage with a catheter. There are various factors that contribute to bladder outlet obstruction/urinary retention (BOO), such as, complications resulting from surgery, diseases, injuries, and aging. Some conditions require only a temporary solution, while others may require a more permanent solution. In addition to the open surgery method of placing a catheter, there are three known methods currently used to resolve urinary retention problems. The first method is known as clean intermittent self-catheterization (CISC). As the name suggests, this method is performed by the patient, using a clean but typically non-sterile technique 3 to 4 times daily. The patient inserts a catheter into their bladder through the urethra at regular intervals over the course of the day. Although this is presently believed to be the preferred method, it can be painful, awkward, depending on available privacy, and otherwise difficult, particularly for modest, elderly and/or incapacitated persons. In addition, complications such as urethral perforation, bladder perforation or stricture formation can occur, particularly in men, and urinary tract infections (UTI) often result from performing the procedure as the procedure is generally "clean" but not sterile.

The second method, and believed to be the most commonly used, is known as a urethral Foley catheterization (UFC). In this process, a physician or nurse inserts a Foley catheter into the bladder through the urethra. The Foley catheter has an internal balloon near its tip that is inflated to maintain the catheter within the bladder. Although this method is the most commonly used, it has many potential problems. With this method, urinary tract infections occur generally at a rate of 3-10 percent per day with an indwelling catheter maintained within the bladder, with about 5 percent of the patients developing bacterial blood infections (bacteremia).

The third method is known as a suprapubic cystostomy (SPC), and it includes two different types of procedures that are performed by a urologist usually employing intravenous (IV) sedation or local anesthesia while usually under hospital care. These procedures can be performed as a standalone procedure or in conjunction with another in unrelated surgical procedures. The first procedure is commonly referred to as a percutaneous or "outside-in" trocar punch procedure, and the second procedure is conversely referred to as a transurethral ("inside-out") or endocystostomy procedure. The SPC methods are predominantly used in the U.S. when long-term drainage is desired, and it is used internationally for both short and long-term drainage. The percutaneous punch "outside-in" procedure is by far the more commonly used method of the two, and it entails inserting a large bore hollow needle through the abdomen and then into the bladder. This procedure requires the bladder to be inflated or distended with water to create a firm abdomen to push against while inserting the hollow bore needle due to tissue resistance. The percutaneous punch method whereby a hollow needle is pushed through the abdomen into the bladder is a blind procedure and relies on physical feel and skill and experience of the physician to safely puncture the bladder. Thereafter, a smaller catheter is inserted through the hollow needle into the bladder. Drawbacks to this method include unreliable drainage due to a high rate of clogging and kinking of the catheter drainage tube. The percutaneous punch method has increased safety issues with high morbidity and mortality rate near 2%, usually from unrecognized puncturing of bowel. These two procedures cannot be safely performed on the morbidly obese patient, a patient population that is increasing, currently estimated to be more than 12 percent of this targeted patient population.

The current transurethral ("inside-out") procedure is performed by inserting a hollow instrument with a blunt tip, commonly referred to as a sound, through the urethra into the bladder. The Sound has a tip that is typically advanced to penetrate through the bladder and abdominal wall and extend outside the abdomen. The surgeon is usually required to make an incision in the abdomen and facia, down to the tip of the sound to allow the blunt tip of the sound to advance through the abdomen exiting the skin. In the cases where the sound tip cannot reach outside the abdomen, the surgeon must make a larger incision in the abdomen with a scalpel to allow for attachment of the catheter while the sound tip resides inside the abdomen. With the sound finally exposed outside the abdomen, a catheter is attached to the end of the sound and drawn back into the bladder and out of the patient through the urethra along with the withdrawn sound. Upon being pulled and exiting the patient through the urethra, the catheter is then detached from the sound and pulled back into the bladder, whereupon a balloon on the catheter is inflated in an effort to maintain the catheter in a desired position within the bladder. Some of the drawbacks to this method include, a relatively high cost of the reusable surgical instruments, requiring sterilization between procedures, the catheter can be difficult to attach to the sound and once attached can disconnect during the procedure requiring the procedure to be repeated, the location of the deflated catheter balloon within the bladder can be difficult to ascertain prior to inflating the catheter balloon, and additionally, it can often not be effectively used to safely perform the procedure on obese and morbidly obese patients.

SUMMARY OF THE INVENTION

A suprapubic transurethral cystotomy apparatus includes an elongate tubular body having a length including a proximal portion and a distal portion inclined relative to one another. The distal portion extends along an axis to an end configured for receipt through a urethra. The apparatus further includes an elongate arm having a first end operably attached to the proximal portion of the tubular body and a second end providing an indicator aligned coaxially with the axis of the distal portion.

According to another aspect of the invention, a method of forming a surgical opening extending through an abdominal wall and into a bladder is provided. The method includes providing an elongate tubular body having a proximal portion and a distal portion and inserting the distal portion through a urethra and into the bladder. Further, providing an elongate arm having a first end and a second end having an indicator establishing an axis and operably attaching the first end of the arm with the proximal portion of the tubular body and positioning the indicator externally over the abdominal wall with the axis arranged in coaxial alignment with the distal portion of the tubular body. Then, puncturing an opening with a cutting member extending along the axis through the bladder and through the abdominal wall.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 11 is a side view showing a penetration depth marker of the apparatus moved adjacent an opening of the urethra;

FIG. 12 is a side view showing the cutting tip penetrating the bladder and abdominal wall;

FIG. 13A is an enlarged cross-sectional view of the capture cup showing the cutting tip attached to the advancement rod and captured in the capture cup;

FIG. 13B is an enlarged cross-sectional view of the capture cup showing the capture cup and the cutting tip removed from the advancement rod and captured in the capture cup;

FIG. 14A is a perspective view of the catheter with a removal tool inserted therein;

FIG. 14B is an enlarged perspective view of a distal end of the catheter;

FIG. 14F is a perspective view of the removal tool;

DETAILED DESCRIPTION OF PRESENTLY PREFERRED EMBODIMENTS

Figure 1:
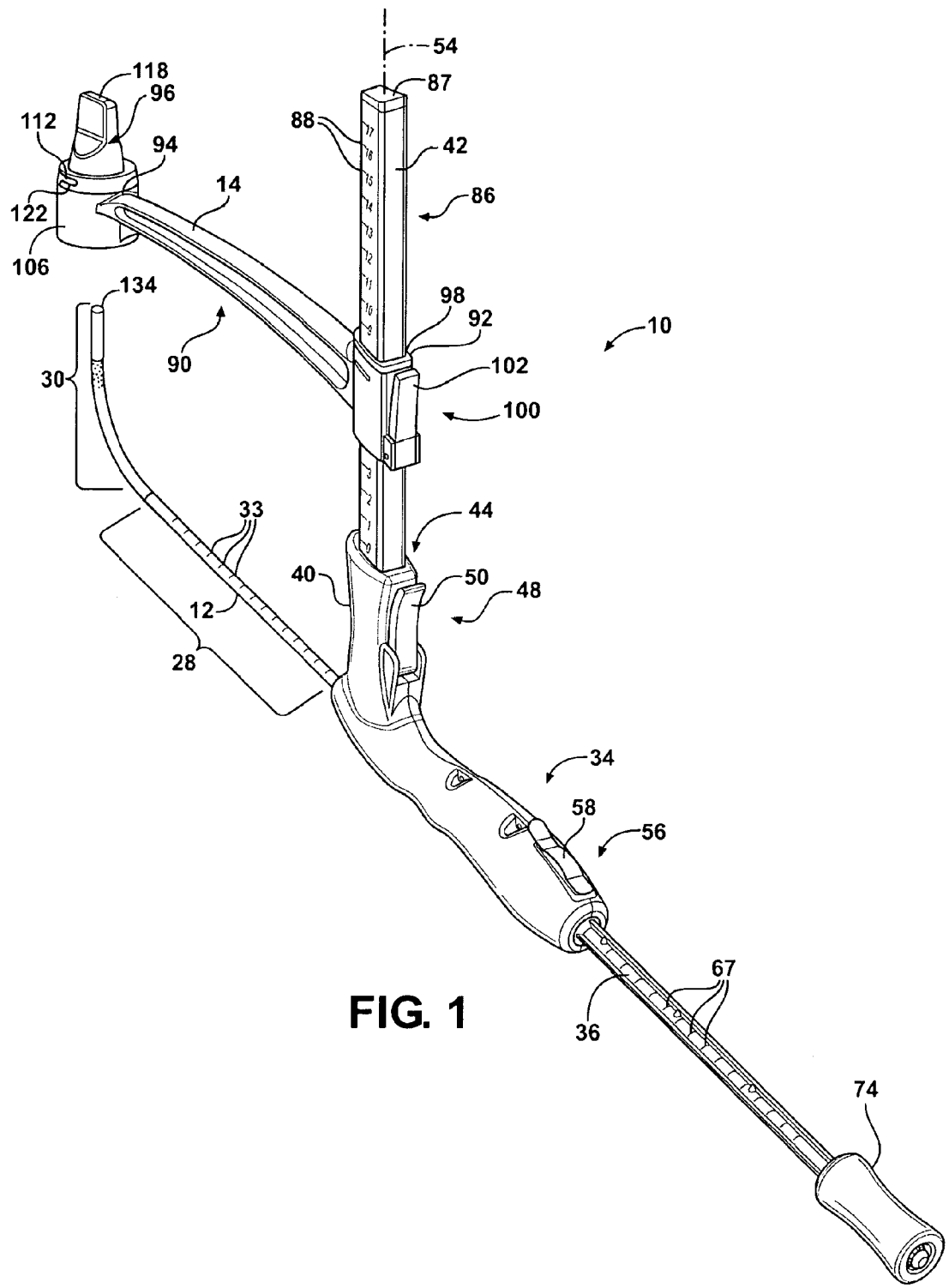
FIG. 1 is a perspective view of a transurethral suprapubic cystostomy apparatus constructed in accordance with one presently preferred embodiment of the invention.
Figure 2:
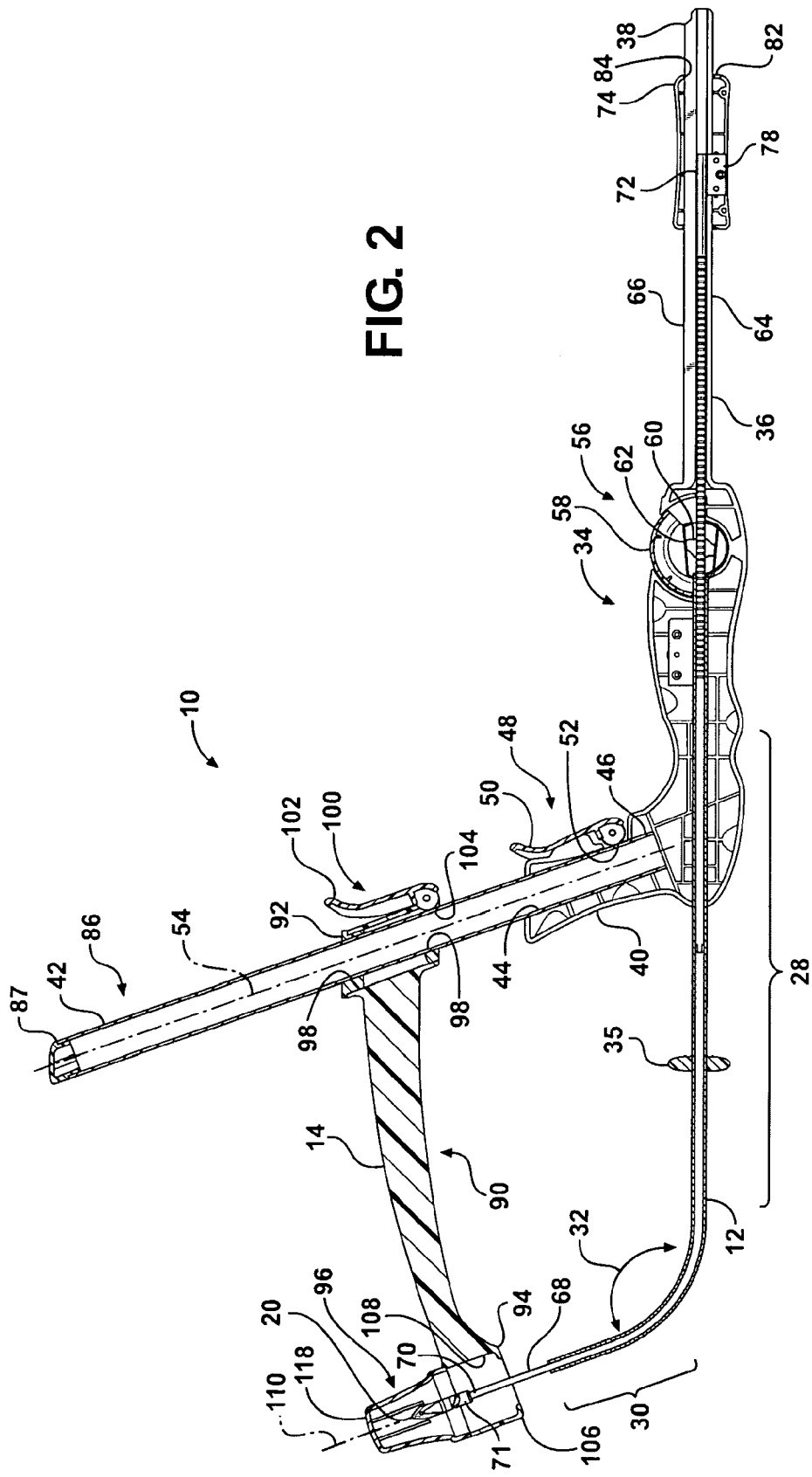
FIG. 2 is a cross-sectional side view of the apparatus.

Referring in more detail to the drawings, FIGS. 1 and 2 illustrate a suprapubic transurethral cystostomy apparatus 10 constructed in accordance with one aspect of the invention. It should be recognized that other embodiments that perform a similar function, in a generally similar way, are contemplated to be within the scope of the invention. For example, the apparatus 10 and its associated individual components can be modified, while having a generally similar construction, and can be further modified to accommodate any size male or female, adult or pediatric patient, including obese and morbidly obese patients. Of course, it will be recognized by those skilled in the art that female and male organs, particularly the urethra, are shaped differently and have differing lengths and diameters, and so, the construction of the apparatus 10 can be varied to accommodate those differences. The apparatus 10 includes an elongate hollow tubular body, generally referred to as a sound 12, and an alignment structure which includes an alignment guide arm 14 and a mast 42, adapted for operable attachment to the sound 12 in a predetermined position relative to the sound 12. The sound 12 is configured for insertion through a urethra 16 into a bladder 18, while the alignment guide arm 14 remains outside the patient to indicate the precise exit location of a trocar, referred to hereafter as cutting tip 20, extending from a the sound 12 through an abdominal wall 22 of the patient. In addition to indicating the precise exit location of the cutting tip 20 through the abdominal wall 22, the alignment guide arm 14 can be positioned to abut the abdominal wall 22 to provide a clamping action against the abdominal wall 22, thereby holding the instrument in place and providing tensile reinforcement of the patient's surface skin to allow the cutting tip 20 to cleanly pierce the skin as it extends outwardly through abdomen without stretching or tearing of the skin. As such, the alignment guide arm 14 allows the surgeon to readily identify the precise location of the cutting tip 20 while in its blind location within the bladder 18, thereby enabling the surgeon to puncture a surgical pathway, referred to hereafter as an opening 24, through the bladder 18 and the abdomen wall 22 at a precise and intended location. Accordingly, the surgeon is provided with an increased level of confidence that the opening 24 formed by the cutting tip 20 is at the desired location, will be clean without tearing, and is further assured that inadvertent damage to internal organs, such as the bowel, is avoided. Upon forming the opening 24, a catheter 26 (FIG. 14) or other surgical instrument can be inserted through the opening 24 and into the bladder 18, depending on the nature of the procedure being performed. Further, the alignment guide arm 14 not only provides a precise exit location for the cutting tip 20, but it can also be used to establish a precise linear path along which to form the opening 24 using an outside-in cut, such as by using an external trocar punch, for example, and extending the external trocar along a line established by the alignment guide arm 14, discussed further below.

Figure 8:
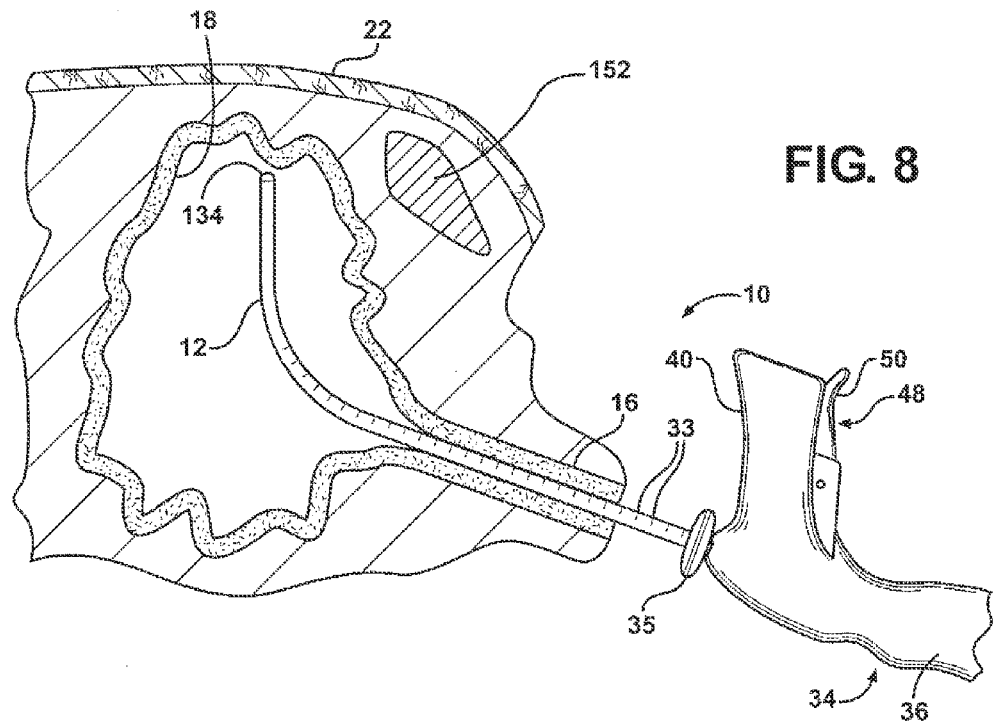
FIG. 8 is a side view of a urethra and bladder showing a sound of the apparatus inserted therein.

As best shown in FIGS. 1 and 2, the sound 12 has a proximal portion 28 and a distal portion 30, with the distal portion 30 being configured for insertion into the bladder 18 through the urethra 16 (e.g., FIG. 8). The proximal portion 28 and the distal portion 30 have respective linear sections that are inclined relative to one another at a predetermined and generally fixed obtuse angle of inclusion 32, such that the angle between the respective linear sections remains generally fixed in use. The proximal portion 28 can have measured indicator markings 33 to indicate to the surgeon the depth of insertion of the sound 12 into the urethra 16. In addition, a penetration depth marker, also referred to as an indicator slide 35 can be disposed on the proximal portion 28 to assist in identifying the depth and location of the sound 12 within the bladder 18 during the procedure. The sound 12 is constructed from a material that can be readily sterilized, such as stainless steel, by way of example and without limitation. It should be recognized that other materials which can be readily sterilized are contemplated and incorporated herein within the scope of the invention, including plastics materials, for example. The sound 12, although constructed from a material capable of being sterilized, is preferably constructed as a disposable, single use instrument.

The proximal portion 28 is fixedly connected to a front handle 34 which has a straight, tubular body 36 extending rearwardly away from the sound 12 to an end 38. The front handle 34 provides a reliable and comfortable location for grasping and manipulating the sound 12. The front handle 34 can be provided having any suitable shape and configuration, depending on the requirements of the surgeon. For example, the front handle 34 can be ergonomically designed for left and right handed physicians and designed for optimal manipulation, control and orientation of the sound 12 while preventing hand slippage when wet and in contact with surgical gloves. Accordingly, it is contemplated that the front handle 34 can be provided having different shapes and contours, as desired. The front handle 34 and tubular body 36 can be molded as single piece halves and then subsequently joined, such as via fasteners, an adhesive or via welding, for example. Of course, the front handle 34 and tubular body 36 can be formed using any suitable plastic or metal materials and processes.

The front handle 34 has an upstanding housing, referred to hereafter as mount sleeve 40, configured for releasable attachment of a straight slide arm, referred to hereafter as mast 42, thereto. As best shown in FIG. 2, the mount sleeve 40 has a pocket 44 sized for close receipt of one end 46 of the mast 42 therein. To facilitate fixing the end 46 of the mast in the pocket 44, the mount sleeve 40 has a releasable mast locking mechanism 48, represented here, by way of example and without limitation, as an over-center cam latch lever 50. The cam latch lever 50 has a cam surface 52 that frictionally engages the mast 42 when the lever 50 is in a depressed, locked position, thereby maintaining the mast 42 in a fixed position within the pocket 44. Otherwise, when the lever 50 is pivoted to a raised, unlocked position, the cam surface 52 is moved out of engagement with the mast 42, thereby allowing the mast 42 to be removed from the pocket 44. The pocket 44 is configured to extend along a straight, linear axis 54, whereby the mast 42, upon being locked within the pocket 44 also extends along the axis 54. The axis 54 is oriented to extend substantially parallel to the distal portion 30 of the sound 12. Accordingly, upon fixing the mast 42 in the mount sleeve 40, the mast 42 and the distal portion 30 of the sound 12 extend parallel or substantially parallel to one another. The angle of the mast 42 extending from the front handle 34 is configured to properly align the alignment guide arm 14 and a capture cup assembly 96 in the proper position to accept the cutting tip 20. This is of great assistance to the surgeon, as the surgeon otherwise would not have a visual location of the cutting tip 20 when inside the bladder 18.

Figure 5:
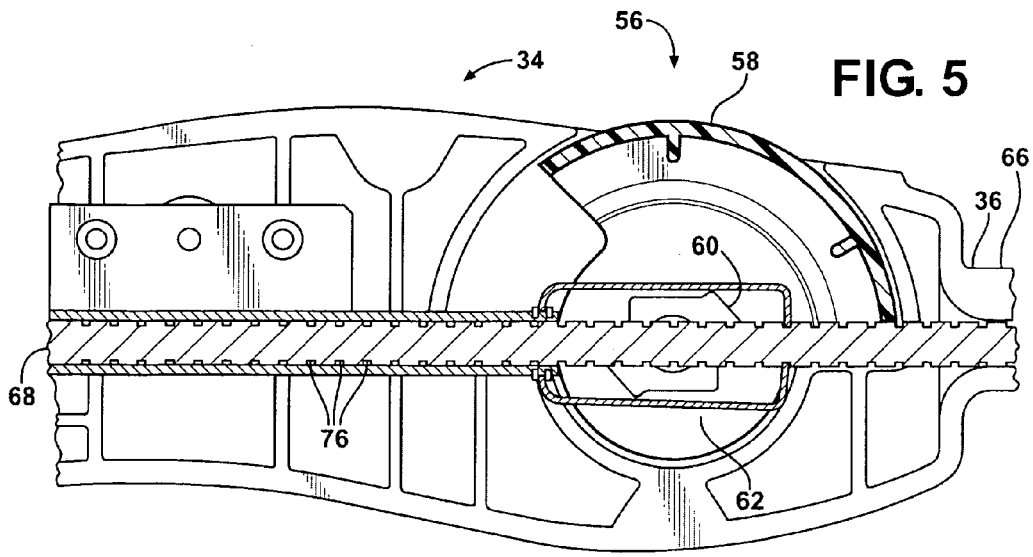
FIG. 5 is an enlarged cross-sectional side view of a front handle shown in a locked position.
Figure 6:
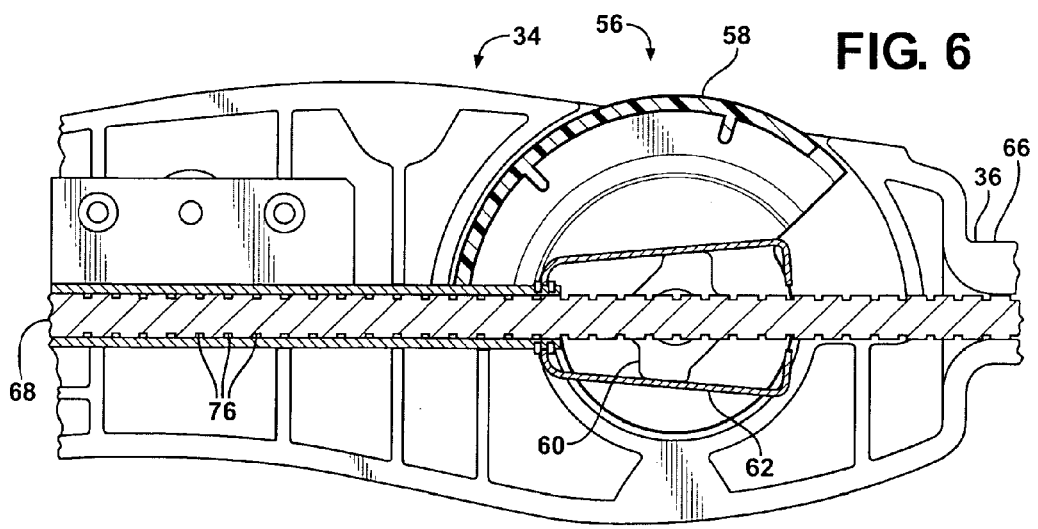
FIG. 6 is an enlarged cross-sectional side view of the front handle shown in an unlocked position.

As best shown in FIGS. 5 and 6, the front handle 34 further includes a cutting tip locking mechanism 56, represented here, by way of example and without limitation, as having a rotatable brake knob or wheel 58, a cam member 60 fixed to the wheel 58 for conjoint rotation therewith, such as by being formed as a single piece of material therewith, and a spring member, referred to hereafter as a brake spring 62. When the wheel 58 is rotated to a locked position, the cutting tip 20 is fixed against relative movement with the sound 12, and when rotated to an unlocked position, the cutting tip 20 is movable relative to the sound 12, discussed further below.

The tubular body 36 extends rear-ward from the rear of the front handle 34 a predetermined distance sufficient to provide the range of movement of the cutting tip 20 desired. It should be recognized that the range of movement of the cutting tip 20 will generally be less for a normal sized patient than for an obese or morbidly obese patient, and that the range of movement of the cutting tip 20 can be provided to accommodate any size patient. The tubular body 36 has tubular wall with an elongate slot 64 extending along its length, wherein the length of the slot 64 corresponds at least to the desired distance of travel of the cutting tip 20. The slot 64 is represented here as extending of the full length of the tubular body 36 along a bottom side thereof. The wall of the tubular body 36 is also represented, by way of example and without limitation, as having an upstanding rib 66 extending along an upper side of the wall diametrically opposite the slot 64. The upper side of the tubular wall preferably has measured scale markings 67 to indicate to the surgeon the distance the cutting tip 20 is extended, discussed further below.

Figure 7:
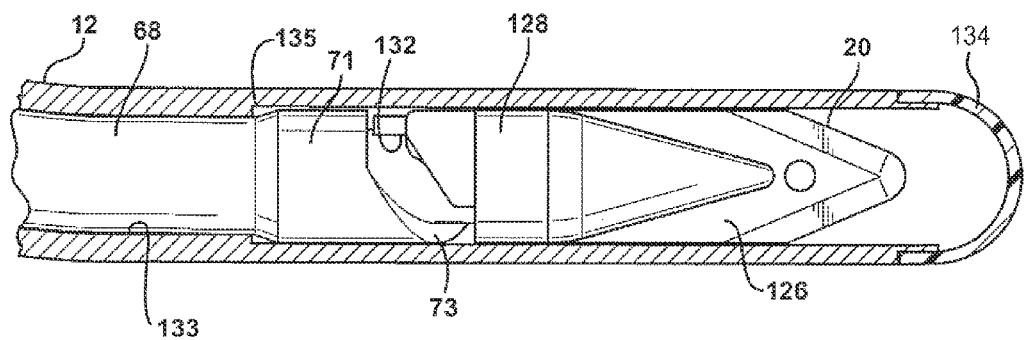
FIG. 7 is an enlarged side view of a cutting tip attached to a collet of an advancement rod of the apparatus of FIG. 1.

The apparatus 10 further includes an advancement member 68, represented here as a flexible coil rod or flat spring member, with a distal end 70 being operably attached to the cutting tip 20 and a proximal end 72 being attached to a rear handle 74 of the apparatus 10. The distal end 70 is represented here as having a connector 71 for selective, releasable attachment of the cutting tip 20 thereto. As best shown in FIG. 7, the connector 71 is a modified bayonet-type connector, for example, having at least one ramped, spiral shaped entry slot 73 terminating at a recessed lock detent. The proximal end 72 is fixed to the rear handle 74, such as by generally narrow connector plate 78 sized to slide through the slot 64. The connector plate 78 can be fixed to the advancement member 68, such as by a weld joint, for example, and to the rear handle 74 via a fastener 80, for example. Accordingly, movement of the rear handle 74 causes conjoint movement of the connector plate 78 and the advancement member 68.

The advancement member 68 can be provided of any suitable material flexible enough to traverse the bend in the sound 12 between the proximal portion 28 and the distal portion 30, while being rigid enough to maintain a straight cutting path through the bladder 18 and abdominal wall 22, such as stainless steel or spring steel, for example. The advancement member 68 can further be provided as a single piece of material or multiple pieces of material joined to one another. The advancement member 68 has a plurality of circumferential notches 76 spaced in axially uniform relation from one another along a proximal or rear portion thereof for operable locking engagement with the brake spring 62. Preferably, the notches 76 extend over the full portion that traverses beneath the cutting tip lock mechanism 56, thereby allowing the cutting tip 20 to be locked in a fully retracted position and in a fully extended position, as well as over a plurality of locations between the fully retracted and extended positions.

Figure 3:
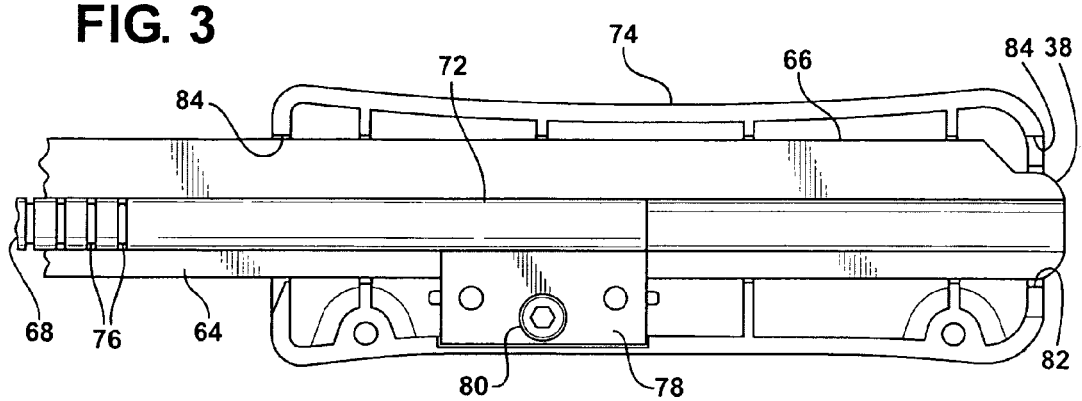
FIG. 3 is an enlarged cross-sectional side view of a rear handle of the apparatus of FIG. 1.
Figure 4:
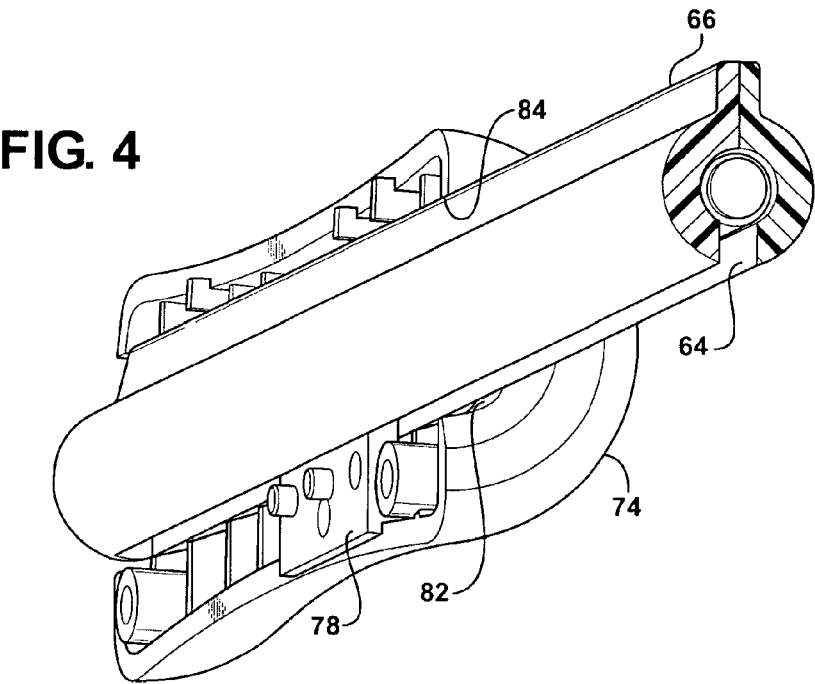
FIG. 4 is an enlarged fragmentary perspective view of a rear handle of the apparatus of FIG. 1.

The rear handle 74 can be provided having any suitable shape and configuration. For example, the rear handle 74 can be ergonomically designed for left and right handed physicians and designed for optimal manipulation, control and orientation of the advancement member 68 and cutting tip 20 while preventing hand slippage when wet and in contact with surgical gloves. The rear handle 74 can be molded as single piece halves, with the halves being subsequently joined, such as via fasteners, an adhesive or via welding, for example, and can be formed using any suitable plastic or metal materials and processes. As shown in FIGS. 2-4, the rear handle 74 is formed having a through passage 82 sized for close sliding receipt over the tubular body 36. The passage 82 can be provided with a recessed notch 84 sized to slidingly receive the upstanding rib 66 therein, thereby preventing rotation of the rear handle 74 about the tubular body 36. This prevents unwanted rotation of the cutting tip 20 while forming the opening through the tissue.

The mast 42 has a straight, elongate body 86 extending between the end 46 received in the pocket 44 of the front handle 34 and an opposite end 87. The body 86 preferably has measured scale markings 88 to facilitate indicating to the surgeon the distance over which the cutting tip 20 generally needs to extend through the abdomen of the patient. The body 86 can be formed as a solid body or a hollowed body using any desired process, such as extrusion, for example, and can be formed of any suitable polymeric or metal material, as desired. The body 86 is represented here as being generally rectangular in lateral cross-section, which assists in maintaining the alignment guide arm 14 in its proper orientation by preventing unwanted relative pivoting between the arm 14 and the positioning mast 42, although any cross-sectional geometry could be used. The body 86 can be provided of any suitable length, and preferably has a length between about 15-20 inches, thereby allowing suitable adjustment of the alignment guide arm 14 on morbidly obese patients.

The alignment guide arm 14 has body 90 that extends between a first end 92 and a second end 94. The first end 92 is configured for operable attachment to the proximal portion 28 of the sound 12 and for sliding receipt along the mast 42. The second end 94 is configured for attachment to the capture cup 96. The first end 92 has a through opening 98 configured for close sliding receipt of the mast body 86. Accordingly, the through opening 98 is shaped having a similar cross-sectional geometry as the mast body 86, though being slightly larger to facilitate sliding movement along the mast body 86. To facilitate releasable locking of the alignment guide arm 14 in a desired fixed position along the mast body 86, the first end 92 has a releasable arm locking mechanism 100, represented here, by way of example and without limitation, as an over-center cam latch lever 102. The cam latch lever 102 has a cam surface 104 that frictionally engages the mast 42 when the lever 102 is in a depressed, locked position, thereby maintaining the alignment guide arm 14 in a fixed position along the mast body 86 at the desired position. Otherwise, when the lever 102 is pivoted to a raised, unlocked position, the cam surface 104 is moved out of engagement with the mast body 86, thereby allowing the alignment guide arm 14 to be slid freely along the length of the mast body 86.

The second end 94 of the alignment guide arm 14 has a semi-annular or annular housing 106 providing a through passage 108 of a predetermined diameter that extends along an axis 110 that is coaxial with the distal portion 30 of the sound 12 when then alignment guide arm 14 is attached to the mast 42, and the mast 42 is received in the mount sleeve 40. The housing 106 is further represented here as the indicator, by way of example and without limitation, as having an upper surface with one or more lateral slots 112 configured to releasably receive the capture cup 96. As shown in FIG. 13A, to facilitate guiding the cutting tip 20 into the capture cup 96, the through passage 108 of the housing 106 can be provided having a funnel shape with an enlarged diameter 114 located adjacent a bottom surface of the housing 106 and a reduced diameter 116 located adjacent the upper surface of the housing 106.

The capture cup 96 has a closed upper portion 118 configured to be easily grasped and rotated, and is represented here, by way of example and without limitation, as having a generally rectangular wall with opposite sides easily graspable between a thumb and index finger. As best shown in FIGS. 13A and 13B, a generally cylindrical, annular wall 120 depends from the upper portion 118, wherein the annular wall 120 is sized for close sliding receipt in the housing 106 of the alignment guide arm 14. Further, the capture cup 96 has one or more fingers 122 extending laterally outwardly for sliding receipt in the slots 112 of the housing 106. The fingers 122 extend outwardly to engage the upper surface of the housing 106, and are received in the slots 112 by rotating the capture cup 96 relative to the housing 106. Accordingly, upon rotating the capture cup 96 in one direction, the fingers 122 slide in the slots 112 and engage a bottom surface of the slots 112, wherein the capture cup 96 is releasably locked to the housing 106, and upon rotating the capture cup 96 in the opposite direction, the fingers 122 exit the slots 112, wherein the capture cup 96 can be removed from the housing.

To facilitate capturing the cutting tip 20 in the capture cup 96, a bore or cavity of the capture cup 96 can be provided with an annular elastomeric wall or sleeve 124, such as an silicone tubing, for example, wherein the sleeve 124 has a slightly reduced diameter from the outer periphery of the cutting tip 20 to cause the cutting tip 20 to cut into the sleeve 124 upon being inserted therein, thereby being captured within the capture cup 96 for hands free disposal. To provide assurance that the cutting tip 20 in fully inserted in the capture cup 96, a stop surface 125 can be provided to abut the cutting tip 20, thereby acting as a positive stop to limit the distance the cutting tip 20 can be inserted into the capture cup 96. Although the capture cup 96 is shown having the fingers 122 for releasable receipt in the slots 112, other attachment mechanisms are contemplated herein, such as a threaded attachment or the capture cup could be formed as a single piece of material with the alignment guide arm 14. To further facilitate releasing the cutting tip 20, a plurality of ribs can extend radially inwardly from the inner surface of the sleeve 124 to provide a bearing surface against the flat cutting blade as a 'stop' when rotating the capture cup 96. This further assures the cutting tip 20 will be rotated conjointly with the capture cup 96 while rotating the capture cup 96.

As best shown in FIGS. 7, 13A and 13B, the cutting tip 20 is constructed having a metal cutting member 126 and a connector 128 depending therefrom. The cutting member 126 is illustrated as having one or more openings 130 to facilitate attachment of the cutting member 126 to the connector 128. The connector 128 can be formed of an polymeric material, and further, can be molded, such as in an injection molding process, for example, to the cutting member 126. The connector 128 has a corresponding number of bayonets or fingers 132 extending laterally outwardly for sliding receipt in the ramped slots 73 in the connector 71. The fingers 132 are configured to lock releasably in the slots 73 by deflecting into recessed detents at the end of the ramped slots 73, and to deflect out of the detents upon applying a suitable torque to the cutting member 126, which can be applied via rotation of the capture cup 96 when the cutting tip 20 is captured therein. The cutting tip 20 can be initially enclosed within a counterbore 133 in the distal end of the sound 12 and/or covered by a relatively soft sheath 134, such as a soft polymeric material attached in flush relation on a reduced outer diameter portion 135 of the distal end portion, e.g. rubber or silicone, to protect the cutting blades of the cutting member 126 and to prevent the inadvertent cutting of tissue while inserting the sound 12 through the urethra 16. Upon moving the cutting tip 20 axially outwardly from the sound 12, the cutting tip 20 can readily penetrate the relatively soft sheath to expose the cutting tip 20 for penetrating through the bladder 18 and out the abdomen wall 22.

Figure 14E:
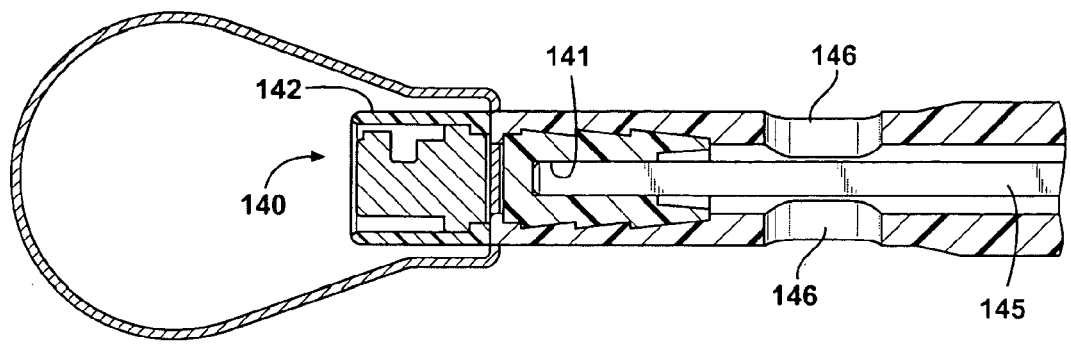
FIG. 14E is a view similar to FIG. 14D with a removal tool inserted into the end.
Figure 14:
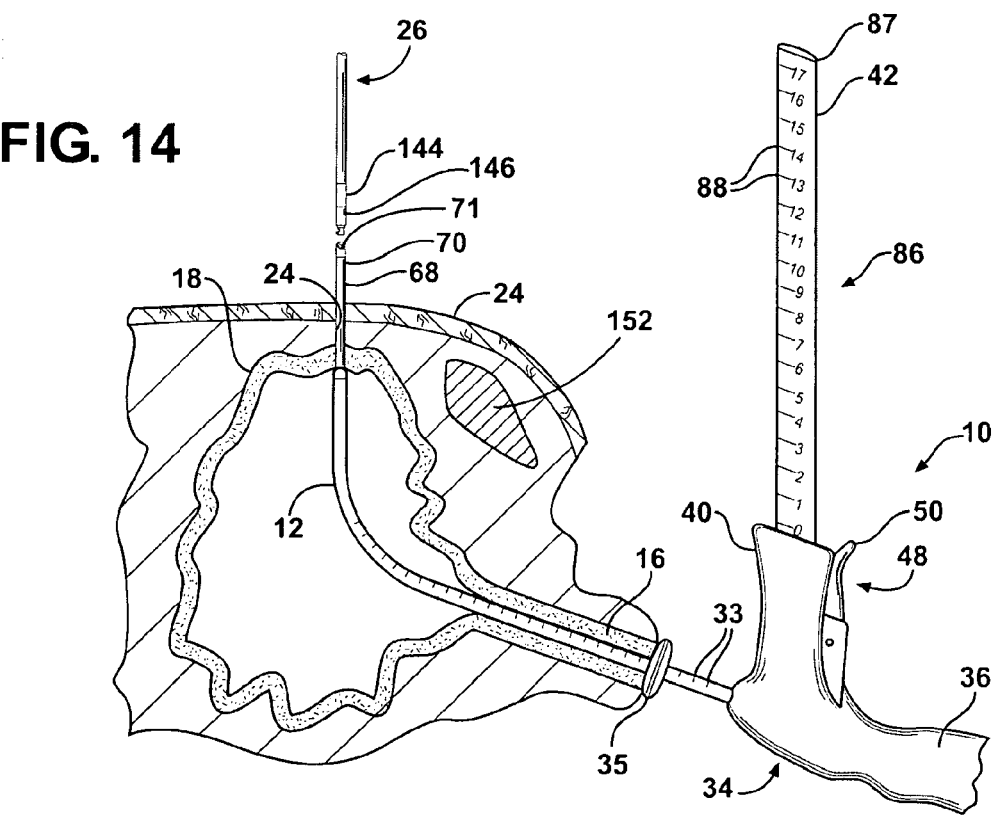
FIG. 14 is a side view showing a catheter about to be attached to the sound via the collet of the advancement rod with the catheter drawn partially through the abdominal wall.
Figure 14C:
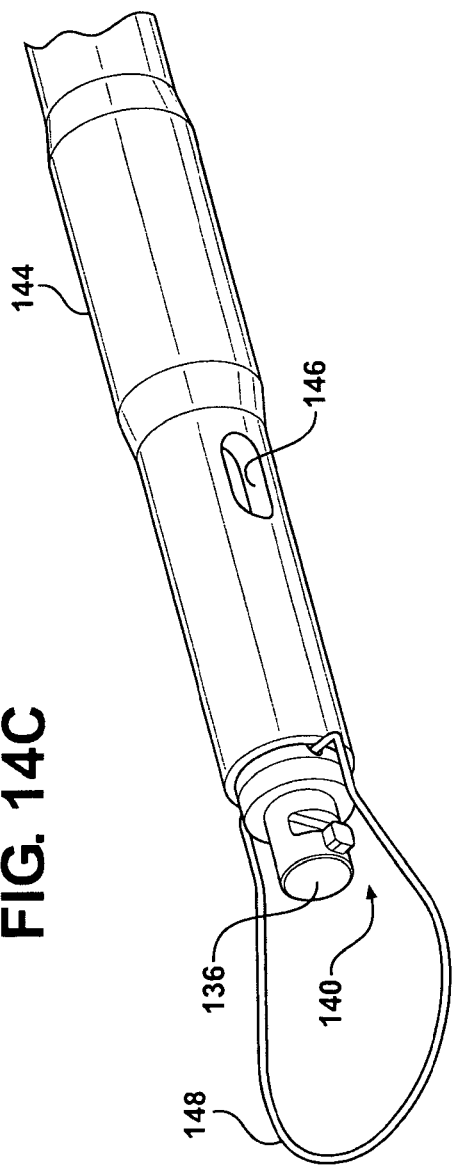
FIG. 14C is an enlarged perspective view of an end of the catheter with a shroud removed from the end.
Figure 14D:
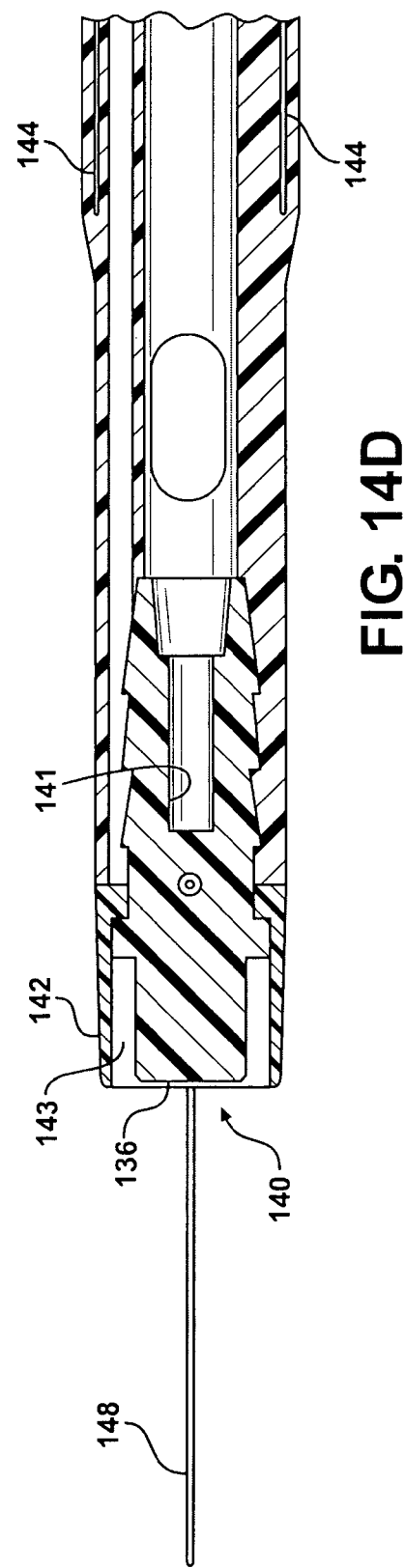
FIG. 14D is an enlarged cross-sectional view of a drainage end of the catheter.

As shown in FIG. 14A, the catheter 26 has a first end 136 configured for operable attachment to the sound 12 via the connector 71 on the advancement member 68 and a second end 138 configured for operable attachment to a fluid collection system. As best shown in FIG. 14C, the first end 136 has a bayonet-type connector 140 configured generally the same as the connector 128 on the cutting tip 20, thereby being attachable and removable via relative rotation, however, as shown in FIG. 14D, the rear of the connector 140 has a non-circular pocket, such as a square pocket 141, for example. The pocket 141 facilitates removing the catheter 26 from the connector 71 of the advancement member 68 via a remove tool 143 having a appropriately shaped removal rod end 145 (FIG. 14E) conforming to the shape of the pocket 141. Accordingly, the rod end 145 here has a square cross-sectional shape. To prevent inadvertent harm to tissue from the connector 140, a shroud 142 is attached to the end 136 of the catheter 26, with the shroud 142 overlying the connector 140 to provide a substantially smooth and soft outer surface about the connector 140. An annular space 143 is provided between the connector 140 and the shroud 142 to allow the connector 71 on the advancement member 68 to be received for attachment to the connector 140 on the catheter 26. The catheter 26 has an inflatable balloon 144 near the first end 136 to selectively maintain the catheter 26 within the bladder 18, and at least one opening 146, represented here by way of example and without limitation as being oval, between the balloon 144 and the first end 136 to provide entry for fluid into the catheter 26 for drainage of the fluid within the bladder 18 through the catheter 26. In addition, the catheter 26 is adapted for releasable attachment of a tether 148 thereto, wherein the tether 148 can be provided as a loop of suture material, for example.

As shown in FIG. 8, the inside-out suprapubic transurethral procedure is initiated by inserting the distal portion 30 of the sound 12 through the urethra 16 and into the bladder 18. During insertion of the sound 12 through the urethra 16, the cutting tip 20 is covered with the sheath 134 to prevent inadvertent damage from occurring to the urethra 16. The mast 42 can be inserted and locked in the mount sleeve 40 and the alignment guide arm 14 can be slid onto the mast 42 and temporarily locked in the desired position via the mast locking mechanism 48.

Figure 9:
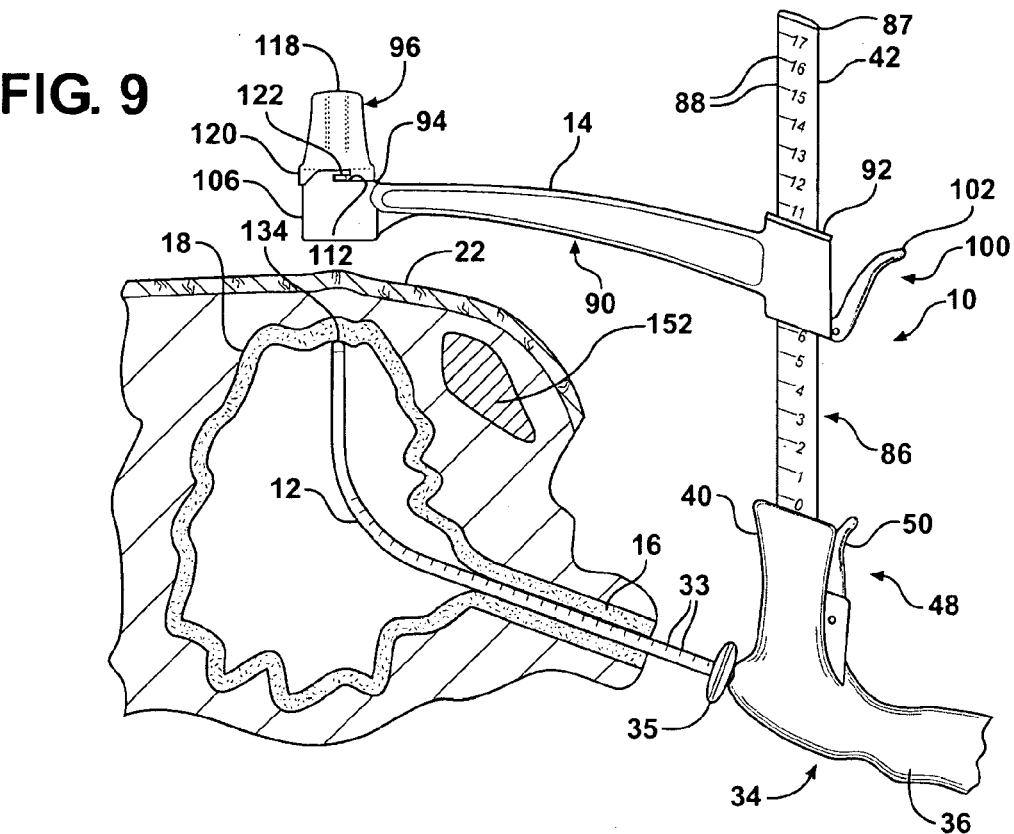
FIG. 9 is a view similar to FIG. 8 showing an alignment guide arm and capture cup of the apparatus positioned above an abdominal wall.

With the alignment guide arm 14 positioned over the abdominal wall 22, an outside-in procedure could be performed, if desired, given the alignment guide arm 14 provides a path directly into the bladder 18. Accordingly, an external trocar punch could be pushed along the axis 110 indicated by the housing 106 through the abdominal wall 22 and into the bladder 18. Otherwise, if performing an inside-out procedure, the capture cup 96 is attached to the housing 106, and the tip or free end of the distal portion 30 is positioned against the inside surface of the bladder 18, generally about 1-2 finger widths above a pubic bone 152, to establish a slight "tenting" of the bladder 18 and abdominal wall 22, as shown in FIG. 9. The tenting facilitates moving the bowel away from the distal portion 30 of the sound 12, and thus, away from the cutting tip 20. With the exception of obese to morbidly obese patients, the tenting is generally observable externally by the surgeon.

Figure 10:
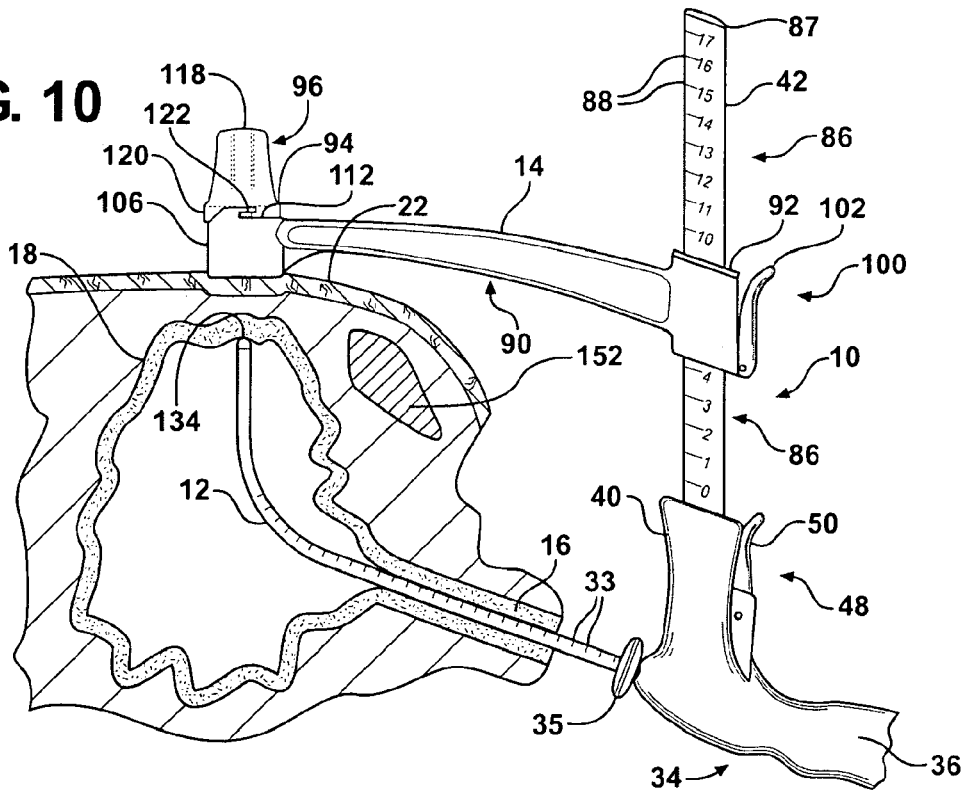
FIG. 10 is a side view showing the capture cup lowered into contact with the abdominal wall.

Next, as shown in FIG. 10, the alignment guide arm 14 can be released from the locked position on the mast 42 and lowered into compressing engagement with the outer skin surface of the abdominal wall 22. With the housing 106 of the alignment guide arm 14 properly positioned against the abdomen wall 22, the mast locking mechanism 48 can again be locked, thereby maintaining the apparatus 10 in the desired position.

Then, as shown in FIG. 11, upon locking the alignment guide arm 14 in the desired location over the abdomen wall 22, the penetration depth marker 35 can be moved forward to the opening of the urethra 16 to prevent further movement of the sound 12. The measurement or indicator markings 33 can be observed by the physician.

Next, as shown in FIG. 12, the cutting tip 20 can be advanced to penetrate through the protective sheath 134, through the bladder 18 and through the abdominal wall 22. This is performed by rotating the wheel 58 of the cutting tip locking mechanism 56 from the locked position to the unlocked position, thereby biasing the brake spring 62 out of engagement with the respective notch 76 in the advancement member 68. Accordingly, the advancement member 68 is free to slide within the tubular body 36 and the sound 12 upon pushing on the rear handle 74. As the rear handle 74 is pushed, the surgeon is able to visually see from the scaled markings 67 on the tubular body 36 how far the advancement member 68, and thus, the cutting tip 20, is being advanced. In addition, the surgeon can readily determine an indication of the distance from the inside of the bladder wall 18 to the outside of the abdomen wall 22 via the measured markings 88 on the mast, and thus, the surgeon knows generally how far the cutting tip 20 must be advanced to penetrate the abdomen wall 22. While being advanced outwardly from the sheath 134 and outwardly, away from the sound 12, the advancement member 68 remains rigid along the length extended away from the sound 12 to allow it to penetrate the abdomen wall 22 in a controlled and substantially straight path such that it remains in constant coaxial alignment with the housing 106 of the alignment guide arm 14 and the capture cup 96.

Figure 13:
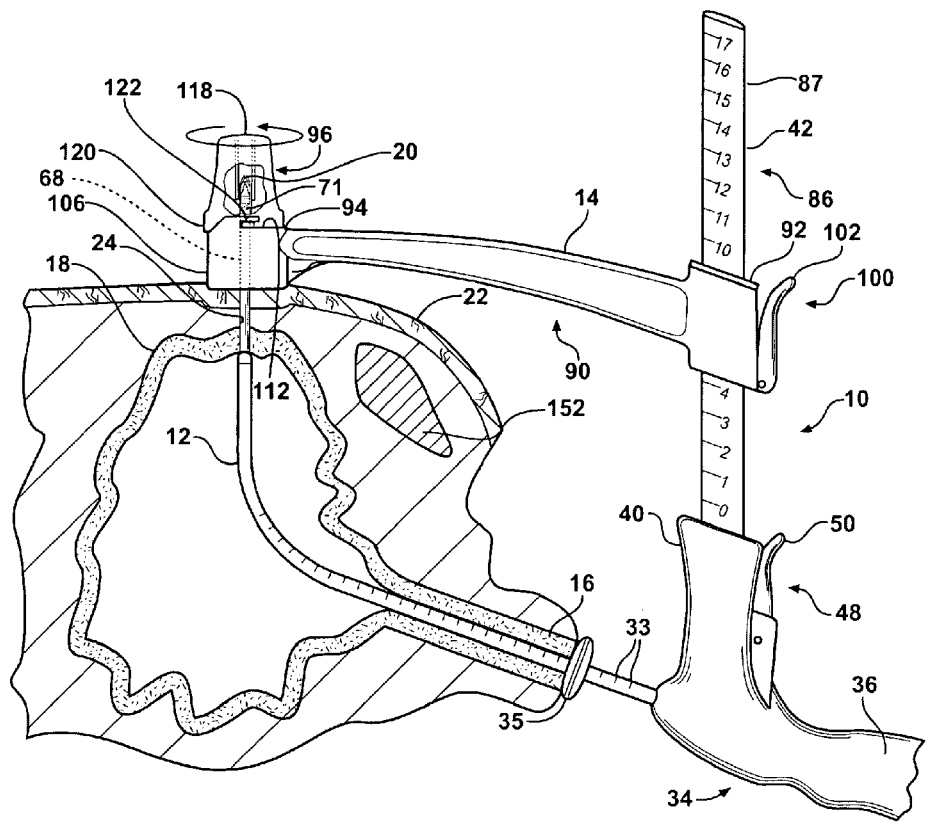
FIG. 13 is a broken away side view showing the cutting tip fully penetrated through the bladder and abdominal wall and received in the capture cup.

As shown in FIGS. 13 and 13A, the cutting tip 20 is then advanced into and captured in the capture cup 96 of the alignment guide arm 14, whereupon the cutting tip 20 can be released in a hands-free procedure and then disposed as captured in the capture cup 96 (FIG. 13B).

Figure 15:
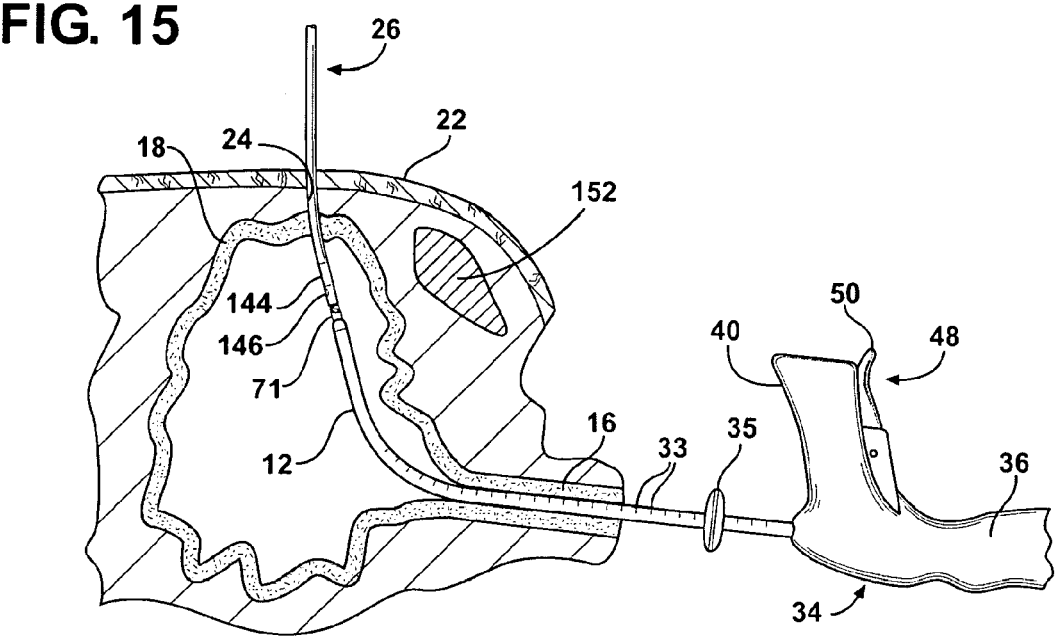
FIG. 15 is a view similar to FIG. 14 showing the catheter drawn into the bladder and the alignment guide arm removed from the sound.

As shown in FIG. 13B, upon the cutting tip 20 being captured in the receptacle 96 and released from the sound 12, the alignment guide arm 14 can then be detached from the mount sleeve 40. Then, as shown in FIG. 14, the end 136 of the catheter 26 can be attached to the connector 71 on the end of the advancement member 68. As shown in FIG. 15, with the catheter 26 operably attached to the sound 12 via the advancement member 68, the catheter 26 can be pulled into the bladder by withdrawing the sound 12 from the urethra 16 and/or by withdrawing the advancement member 68 via pulling on the rear handle 74. The depth marker 35 on the sound 12 located at the opening of the urethra 16 can assist the surgeon in identifying how far the sound 12 needs to be withdrawn in order to ensure the end 136 and balloon 144 of catheter 26 are located sufficiently within the bladder 18 prior to inflating the balloon 144.

Figure 16:
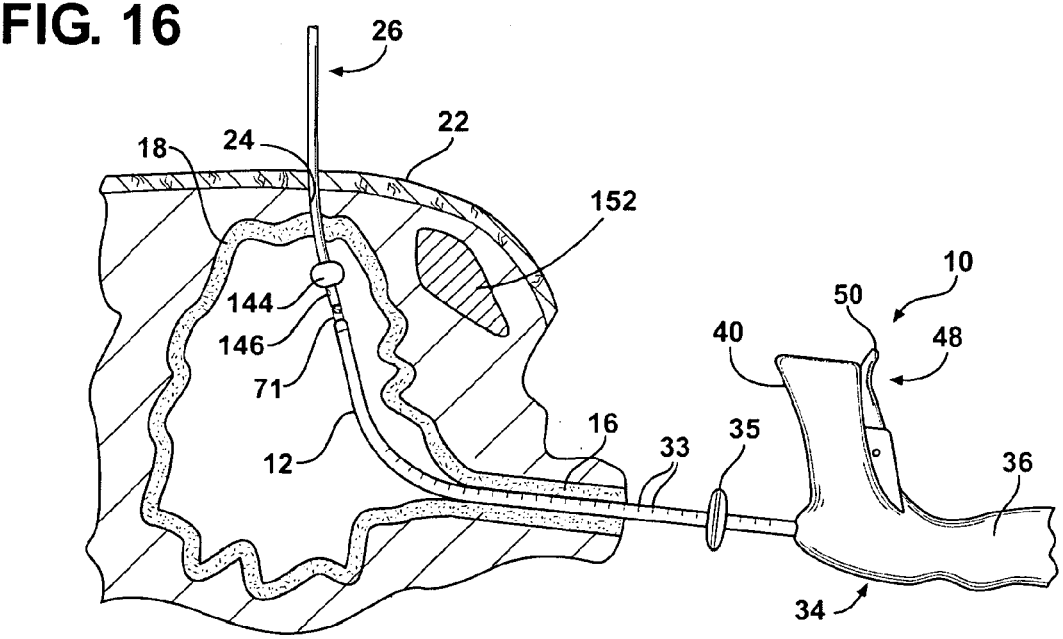
FIG. 16 is a view similar to FIG. 15 showing a balloon of the catheter inflated.

As shown in FIG. 16, with the sound 12 and/or advancement member 68 having been drawn a sufficient distance outwardly from the urethra 16 to ensure the catheter 26 is received properly in the bladder 18, as noted by the distance between the urethra opening and the penetration depth marker 35, the balloon 144 of the catheter 26 is inflated with fluid via a syringe 88 at or adjacent to the second end 84 of the catheter 26.

Figure 17:
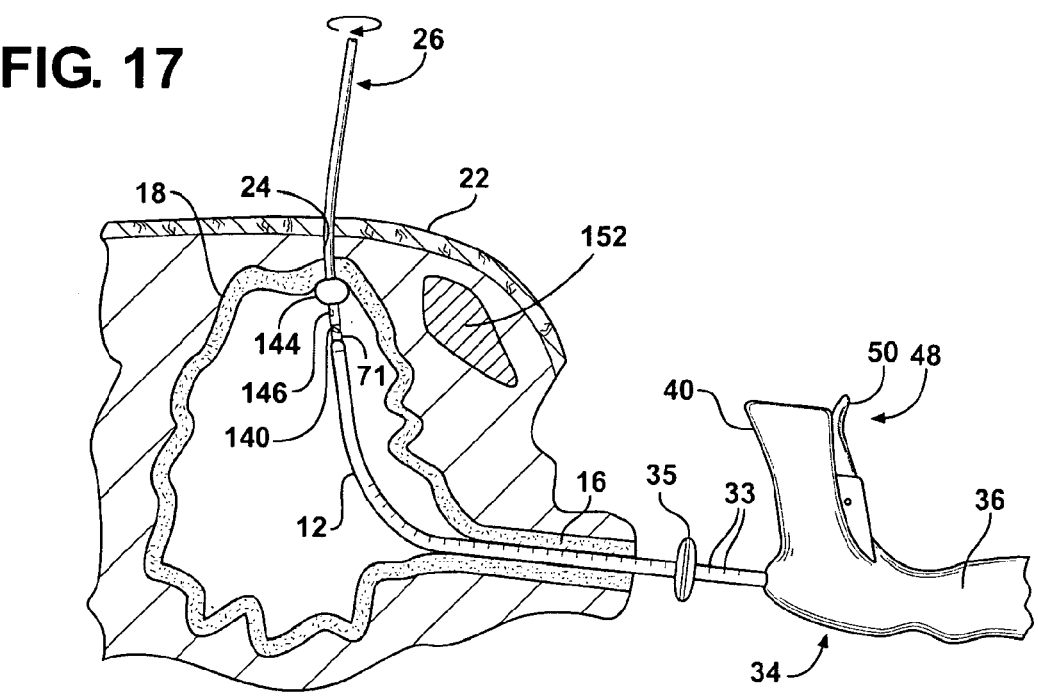
FIG. 17 is a view similar to FIG. 16 showing the inflated balloon drawn back into abutment with the bladder wall.

As shown in FIG. 17, the inflated balloon 144 is then manipulated into seated engagement with the surgically cut opening in the bladder 18 by pulling or otherwise withdrawing the catheter 26 slightly outwardly from the abdominal wall 22, while still attached to the advancement member 68.

Figure 18:
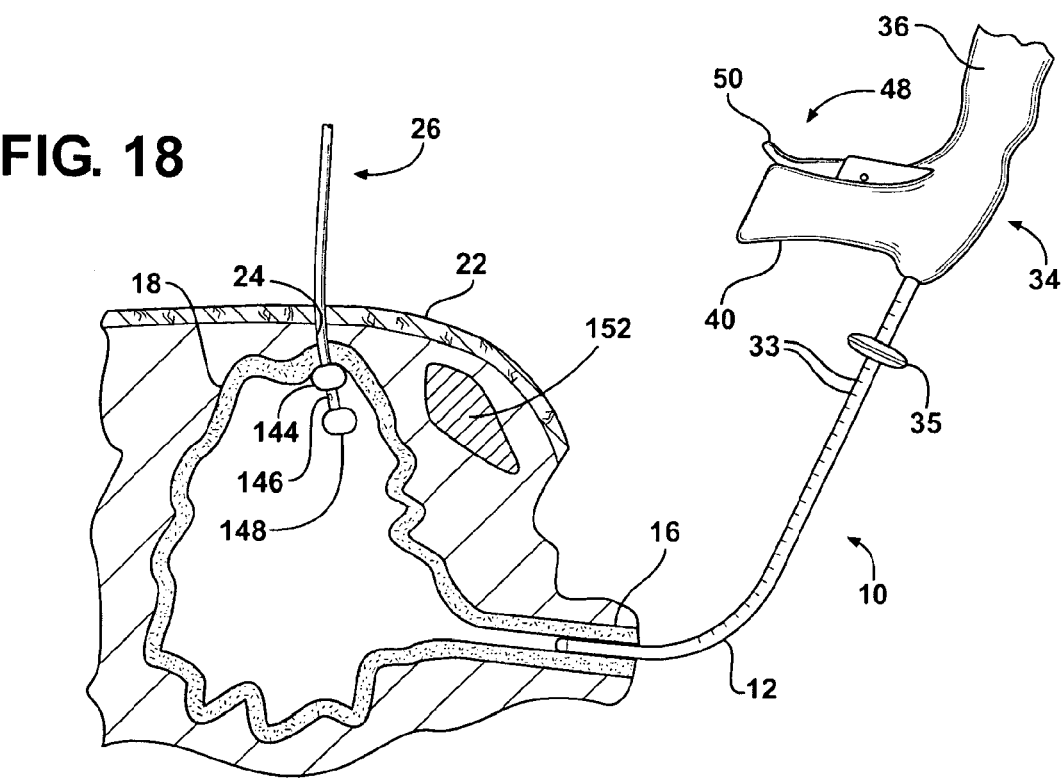
FIG. 18 is a view similar to FIG. 17 showing the catheter detached from the collet of the advancement rod and the sound being withdrawn from the urethra.

Then, as shown in FIG. 18, once the surgeon has verified that the balloon 144 is properly seated against the inner surface of the bladder wall 18, and that proper drainage is flowing through the catheter 26, catheter 26 is detached from the advancement member 68, and the sound 12 is then gently withdrawn from the urethra 16. As discussed above, the detachment of the catheter 26 from the advancement member 68 is facilitated by use of the removal tool 143. By inserting the rod of the removal tool 143 through the length of the catheter 26, and inserting the appropriately configured rod end 145 into the pocket 141 of the connector 140, the removal tool 143 can be rotated in the counter-clockwise direction to impart relative rotation between the connectors 71, 140, thereby causing the catheter to become disconnected from the advancement member while the connectors 71, 140 are in the bladder 18. Meanwhile, though the sound 12 and advancement member 68 are free for removal through the urethra 16, the catheter 26 remains partially deployed in the bladder 18 with the balloon 144 in seated engagement with the inner surface of the bladder wall 18.

Obviously, many modifications and variations of the present invention are possible in light of the above teachings. It is, therefore, to be understood that within the scope of the appended claims, the invention may be practiced otherwise than as specifically described.

What is claimed is:

1. A method of forming a surgical opening from a bladder through an abdominal wall, comprising:
   providing an elongate tubular body having a proximal portion and a distal portion extending along a linear axis;
   inserting the distal portion through a urethra and into the bladder to a position at which the surgical opening is formed;
   providing an elongate arm having a first end and a second end having an indicator establishing an axis;
   operably attaching the first end of the arm with the proximal portion of the tubular body and positioning the second end of the arm to locate the indicator externally over the abdominal wall with the axis of the indicator arranged in coaxial alignment with the linear axis of the distal portion of the tubular body;
   puncturing the surgical opening by extending an advancement member out of the distal portion of the tubular body and along the linear axis of the distal portion of the tubular body through the abdominal wall to the indicator; and
   indicating with the indicator the position of the linear axis on the external abdominal wall by maintaining the axis of the indicator in coaxial alignment with the linear axis of the distal portion of the tubular body while the advancement member extends from the tubular body through the abdominal wall to puncture the surgical opening.

2. A method as defined in claim 1, further including attaching a cutting member to the advancement member and sliding the advancement member and the attached cutting member out of the tubular body to puncture the surgical opening.

3. A method as defined in claim 2 further including removing the cutting member from the advancement member after puncturing the surgical opening and attaching a catheter to the advancement member externally of the abdominal wall and drawing the catheter through the surgical opening into the bladder.

4. A method as defined in claim 3 further including disconnecting the catheter from the advancement member inside the bladder.

5. A method as defined in claim 1 further comprising:
   permitting adjustable movement of the indicator along a range of distances along the coaxially aligned axes of the indicator and the distal portion of the tubular body while maintaining the coaxial alignment.

6. A method of forming a surgical opening through an abdominal wall from a bladder using a suprapubic transurethral cystotomy apparatus, the cystostomy apparatus comprising an elongate tubular body and an advancement member and an alignment structure, the tubular body having a proximal portion and a distal portion extending along a linear axis, the advancement member movably positioned to move from the tubular body, the alignment structure connecting to the proximal portion of the tubular body and having an indicator which indicates the linear axis from the distal portion of the tubular body, the method comprising:
   inserting the distal portion of the tubular body through a urethra and into the bladder while the proximal portion of the tubular body and the connected alignment structure remain outside of the urethra;
   locating the indicator externally over the abdominal wall in coaxial alignment with the linear axis;
   manipulating the proximal portion of the tubular body outside of the urethra to position a distal tip of the distal portion at a predetermined location within the bladder at which the surgical opening will communicate with the bladder;
   advancing the advancement member from the distal portion of the tubular body along the linear axis while the distal tip is positioned at the predetermined location to form the surgical opening through the abdominal wall between the distal tip and the indicator; and
   indicating with the indicator the position of the linear axis at the external abdominal wall by maintaining the indicator located in coaxial alignment with the linear axis as the advancement member advances from the distal tip through the abdominal wall to form the surgical opening.

7. A method as defined in claim 6, further comprising:
   manipulating the proximal portion of the tubular body and the connected alignment structure to position the indicator externally over the abdominal wall to indicate the linear axis at a predetermined location where the surgical opening will extend through the external abdominal wall, before forming the surgical opening.

8. A method as defined in claim 7, further comprising:
   moving the indicator along the linear axis while maintaining the coaxial alignment of the indicator with the linear axis externally of the abdominal wall to accommodate a thickness of the abdominal wall at the predetermined location where the surgical opening will extend from the external abdominal wall.

9. A method as defined in claim 6, wherein the distal portion is linear and inclined relative to the proximal portion of the tubular body and the distal portion defines the linear axis along the distal portion through the distal tip, and the connected alignment structure positions the indicator in coaxial alignment with the linear axis.

10. A method as defined in claim 9, wherein the cystotomy apparatus further comprises a cutting member connected at a distal end of the advancement member, and the method further comprises:
moving the advancement member to advance the cutting member from the distal tip of the tubular body along the linear axis through the abdominal wall.

11. A method as defined in claim 10, wherein a proximal end of the advancement member extends from the proximal portion of the tubular member, and the method further comprises:
moving the advancement member to form the surgical opening by manipulating the proximal end of the advancement member extending from the proximal portion of the tubular member.

12. A method as defined in claim 10, further comprising:
disconnecting the cutting member from the distal end of the advancement member after forming the surgical opening and while the distal end of the advancement member remains external of the abdominal wall;
connecting a surgical instrument to the distal end of the advancement member while advancement member extends through the surgical opening and the distal end of the advancement member remains external of the abdominal wall; and
retracting the advancement member to guide the connected surgical instrument into the surgical opening.

13. A method as defined in claim 12, further comprising:
retracting the advancement member to guide a portion of the connected surgical instrument through the surgical opening and into the bladder; and
disconnecting the surgical instrument from the distal end of the advancement member inside the bladder.

14. A method as defined in claim 10, further comprising:
capturing the cutting member in a capture device at the exterior of the abdominal wall after the cutting member completes formation of the surgical opening.

15. A method as defined in claim 14, further comprising:
positioning the capture device at the linear axis at the exterior abdominal wall.

16. A method as defined in claim 15, further comprising:
disconnecting the cutting member from the advancement member while the cutting member is captured within the capture device.

17. A method as defined in claim 15, further comprising:
positioning the capture device by connecting the capture device to the alignment structure.

18. A method as defined in claim 17, further comprising:
disconnecting the cutting member from the advancement member and substantially simultaneously disconnecting the capture device from the alignment structure while the cutting member is captured within the capture device.

19. A method as defined in claim 6, further comprising:
moving the indicator along a range of distances along the linear axis at the exterior abdominal wall while maintaining the coaxial alignment of the indicator with the linear axis to accommodate a thickness of the abdominal wall at the location where the surgical opening is formed.

20. A method of forming a surgical opening extending through an abdominal wall and a bladder, comprising:
inserting a cutting member through a urethra and into the bladder to a predetermined location within the bladder at which the surgical opening will communicate with the bladder;
establishing a linear axis from the cutting member through the abdominal wall along which the surgical opening will extend when formed;
manipulating an indicator externally above the abdominal wall to a predetermined location at the exterior abdominal wall where the surgical opening will extend through the external abdominal wall;
maintaining the indicator in a coaxial relationship with the linear axis while manipulating the cutting member and forming the surgical opening;
advancing the cutting member from the predetermined location within the bladder along the linear axis through the abdominal wall to the indicator to form the surgical opening; and
indicating with the indicator the position of the linear axis on the external abdominal wall while maintaining the indicator in the coaxial relationship with the linear axis as the cutting member advances through the abdominal wall.

21. A method as defined in claim 20, further comprising:
manipulating the indicator along the linear axis while maintaining the coaxial alignment of the indicator with the linear axis externally of the abdominal wall to accommodate a thickness of the abdominal wall.

* * * * *